(12) United States Patent
Parthasaradhi et al.

(10) Patent No.: US 7,446,203 B2
(45) Date of Patent: Nov. 4, 2008

(54) PREPARATION OF INTERMEDIATES FOR ACETYCHOLINESTERASE INHIBITORS

(75) Inventors: Reddy Bandi Parthasaradhi, Hyderabad (IN); Reddy Kura Rathnakar, Hyderabad (IN); Reddy Rapolu Raji, Hyderabad (IN); Reddy Dasari Muralidhara, Hyderabad (IN)

(73) Assignee: Hetero Drugs Limited, Hyderabad, Andrapradesh (IN)

( * ) Notice: Subject to any disclaimer, the term of this patent is extended or adjusted under 35 U.S.C. 154(b) by 685 days.

(21) Appl. No.: 10/510,410

(22) PCT Filed: Jul. 1, 2003

(86) PCT No.: PCT/IN03/00232

§ 371 (c)(1),
(2), (4) Date: Oct. 6, 2004

(87) PCT Pub. No.: WO2005/003092

PCT Pub. Date: Jan. 13, 2005

(65) Prior Publication Data

US 2006/0041140 A1   Feb. 23, 2006

(51) Int. Cl.
*C07D 211/06* (2006.01)
(52) U.S. Cl. .................................................. 546/205
(58) Field of Classification Search ................. 546/205
See application file for complete search history.

(56) References Cited

U.S. PATENT DOCUMENTS

| | | | |
|---|---|---|---|
| 4,357,337 A * | 11/1982 | Dubroeucq et al. | 514/319 |
| 4,895,841 A | 1/1990 | Sugimoto | |
| 5,606,064 A | 2/1997 | Lensky | |
| 6,252,081 B1 | 6/2001 | Iimura | |
| 6,277,866 B1 | 8/2001 | Takeuchi et al. | |
| 6,492,522 B1 | 12/2002 | Gutman | |
| 6,649,765 B1 | 11/2003 | Vidyadhar | |

FOREIGN PATENT DOCUMENTS

| | | |
|---|---|---|
| EP | 296560 | 12/1988 |
| WO | WO 9722584 | 6/1997 |
| WO | WO 99/36405 | 7/1999 |

OTHER PUBLICATIONS

PCT International Search Report Dated Jul. 1, 2003.
J. Heterocyclic Chem. 2(4), 366-370 (1965).

* cited by examiner

*Primary Examiner*—Celia Chang
(74) *Attorney, Agent, or Firm*—Caesar, Rivise, Bernstein, Cohen & Pokotilow, Ltd.

(57) ABSTRACT

A simple, industrial process for the preparation of the intermediates of acetyl cholinesterase inhibitors is provided. Thus, for example, 5,6-dimethoxy-2-(4-pyridyl)methyl-1-indanone is hydrogenated using platinum oxide catalyst in the presence of hydrochloric acid under a pressure of 2 bars to give 4-[(5,6-dimethoxy-1-indanon)-2-yl]methylpiperidine hydrochloride, which is then converted to donepezil hydrochloride, an acetyl cholinesterase inhibitor.

9 Claims, No Drawings

PREPARATION OF INTERMEDIATES FOR ACETYCHOLINESTERASE INHIBITORS

FIELD OF THE INVENTION

The present invention provides a simple and cost effective process for the preparation of intermediates for acetyl cholinesterase inhibitors.

BACKGROUND OF THE INVENTION

U.S. Pat. No. 4,895,841 and U.S. Pat. No. 6,277,866 disclosed piperidine derivatives having excellent anti acetyl cholinesterase activity. These compounds are effective for treatment and prevention of diseases such as Alzheimer senile dementia, Huntington's chorea, Pick's disease and ataxia. Of these compounds, donepezil hydrochloride, 1-benzyl-4-[(5,6-dimethoxy-1-indanon-2-yl)methyl]piperidine hydrochloride is a well known acetyl cholinesterase inhibitor and is on the market as Aricept for the treatment of Alzheimer disease.

According to the process disclosed in U.S. Pat. No. 4,895,841, 5,6-dimethoxy-1-indanone was condensed with 1-benzyl-4-formylpiperidine in the presence of lithium diisopropylamide to give 5,6-dimethoxy-2-[[1-benzyl-4-piperidinyl]methylene]-1-indanone, which was then reduced with platinum oxide catalyst to give donepezil.

1-Benzyl-4-formylpiperidine is not available and difficult to synthesize commercially. Moreover the combined yield is very low.

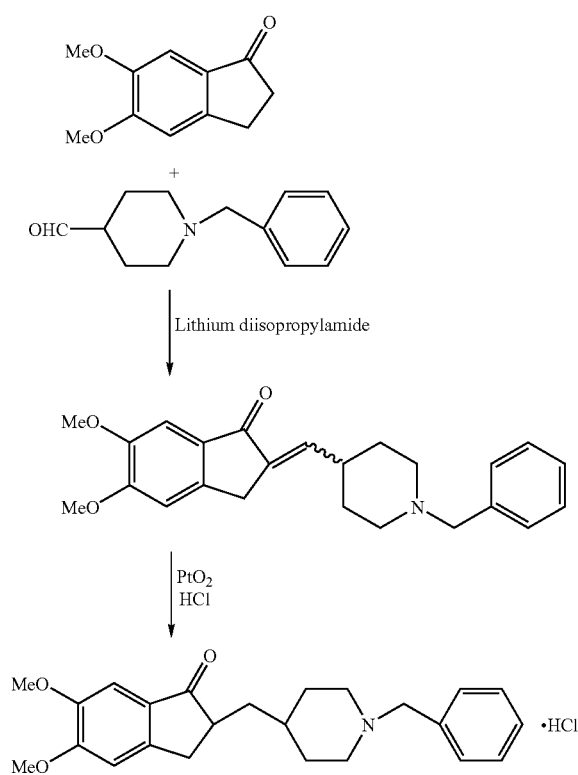

U.S. Pat. No. 5,606,064 disclosed a process for the preparation of donepezil. 5,6-dimethoxy-1-indanone was condensed with pyridin-4-aldehyde to give 5,6-dimethoxy-2-(pyridin-4-yl)methyleneindan-1-one, reacted with benzyl bromide to give 1-benzyl-4-(5,6-dimethoxyindan-1-on-2-ylidene)methylpyridinium bromide and then, hydrogenated in the presence of platinum oxide catalyst to yield donepezil. The yield of the hydrogenation of pyridinium salt is 81%.

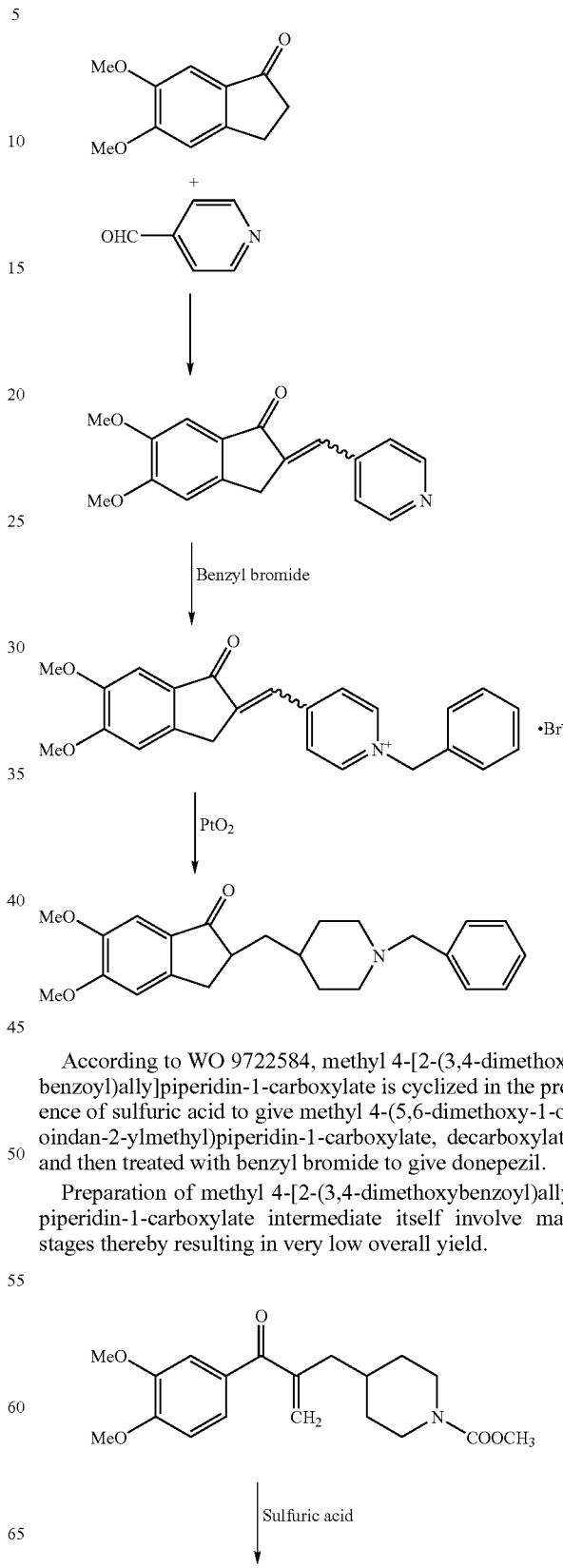

According to WO 9722584, methyl 4-[2-(3,4-dimethoxybenzoyl)ally]piperidin-1-carboxylate is cyclized in the presence of sulfuric acid to give methyl 4-(5,6-dimethoxy-1-oxoindan-2-ylmethyl)piperidin-1-carboxylate, decarboxylated and then treated with benzyl bromide to give donepezil.

Preparation of methyl 4-[2-(3,4-dimethoxybenzoyl)allyl]piperidin-1-carboxylate intermediate itself involve many stages thereby resulting in very low overall yield.

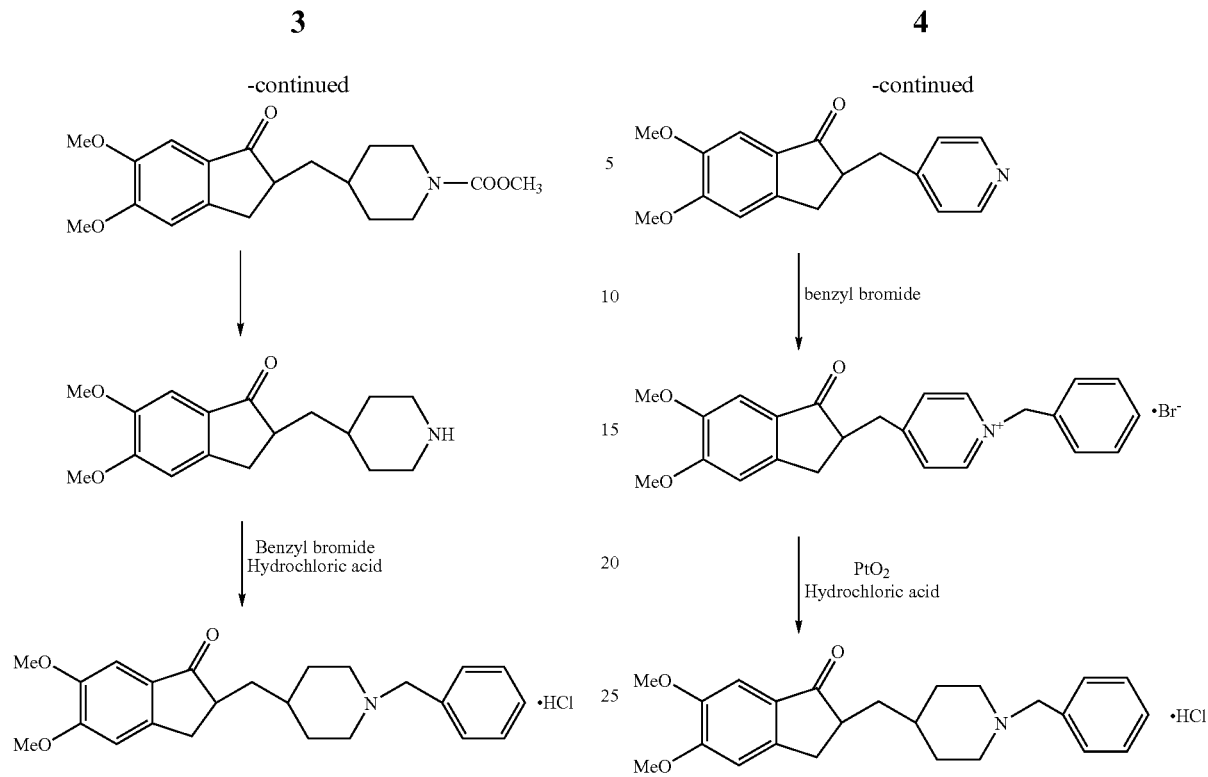

According to U.S. Pat. No. 6,252,081, 5,6-dimethoxy-2-methoxycarbonyl-1-indanone is reacted with 4-pyridinylmethyl chloride to give 5,6-dimethoxy-2-(4-pyridyl)methoyl-2-methoxycarbonyl-1-indanone, decarboxylated to give 5,6-dimethoxy-2-(4-pyridyl)methyl-1-indanone then, reacted with benzyl bromide to give 1-benzyl-4-[(5,6-dimethoxy-1-indanon)-2-yl]methylpyridinium bromide followed by catalytic hydrogenation to yield donepezil.

The process involves introduction of methoxy carbonyl group and decarboxylation steps, thereby making the process very lengthy.

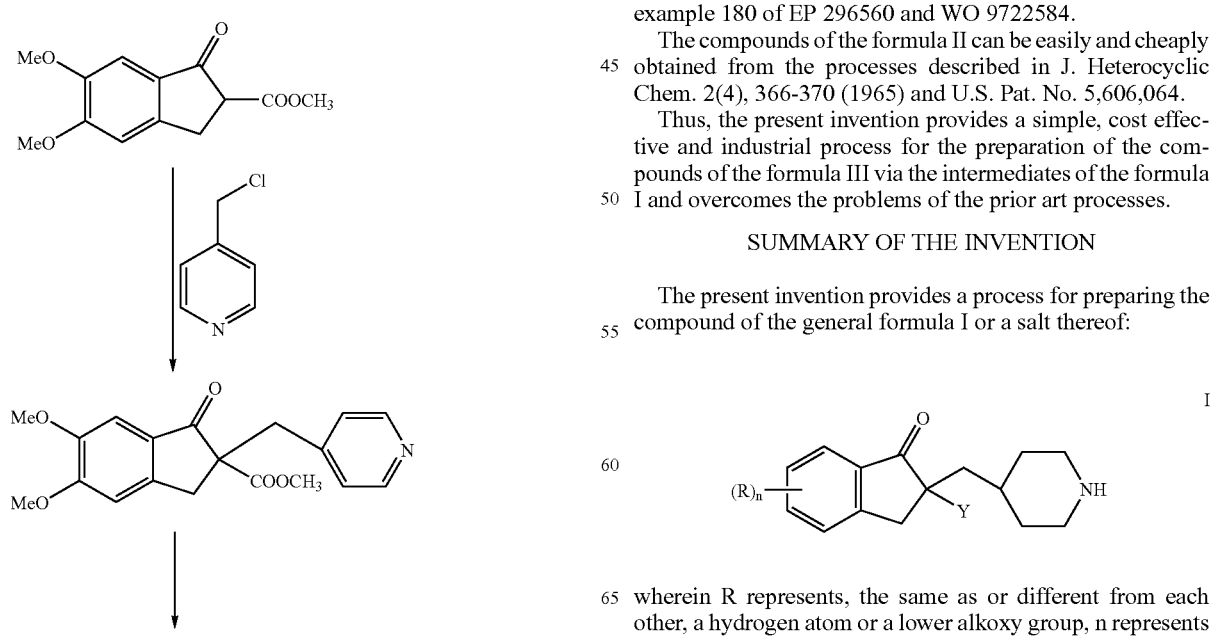

Indanone derivatives of the formula I are useful intermediates for the preparation of acetyl cholinesterase inhibitors of the formula III. The major problem with the preparation of the compounds of the formula I by the catalytic hydrogenation of the compound of the formula II is that high pressures are required and that under these conditions carbonyl group is also reduced to alcohol.

We have found that the compounds of the formula II can be selectively hydrogenated to yield the compounds of the formula I using hydrogenating catalyst under a suitable condition. The yields and purities are found to be very good.

The intermediates of the formula I can be converted to the compounds of formula III by the method described in example 180 of EP 296560 and WO 9722584.

The compounds of the formula II can be easily and cheaply obtained from the processes described in J. Heterocyclic Chem. 2(4), 366-370 (1965) and U.S. Pat. No. 5,606,064.

Thus, the present invention provides a simple, cost effective and industrial process for the preparation of the compounds of the formula III via the intermediates of the formula I and overcomes the problems of the prior art processes.

SUMMARY OF THE INVENTION

The present invention provides a process for preparing the compound of the general formula I or a salt thereof:

wherein R represents, the same as or different from each other, a hydrogen atom or a lower alkoxy group, n represents an integer of 1 to 4 and Y represents H or F, which comprises the hydrogenation of the compound of the general formula II:

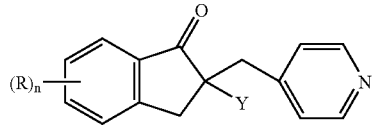

wherein R, n and Y have the same meaning as defined above, with hydrogen using platinum oxide, palladium-carbon, raney nickel or ruthenium oxide catalyst in the presence of an acid under a hydrogen pressure of 1 to 10 bars and optionally converting the compound of the formula I to the salt.

Lower alkoxy group herein means a straight or branched lower alkyl group having 1 to 6 carbon atoms bonded with oxygen atom.

Preferably, 0.1 to 10 moles of the acid per mole of the compound of formula II more preferably 0.5 to 5 moles of the acid per mole of the compound of formula II is used.

Preferable acids are hydrochloric acid, sulfuric acid, phosphoric acid and acetic acid.

Hydrogen pressure is maintained preferably between about 1 to 6 bars and more preferably between about 1 to 4 bars.

The catalyst is usually present in an amount from about 0.01 to about 25 weight-percent, and preferably from about 0.1 to about 10 weight-percent, based on the compound of the formula II. Platinum oxide is the preferred catalyst.

Preferable salt of the compound of the formula I is hydrochloric acid salt.

The compounds of the formula I, wherein n is 1-3, R is methoxy or ethoxy and Y is H are preferred compounds.

The present invention also provides the preparation of an acetyl cholinesterase inhibitor of the formula III:

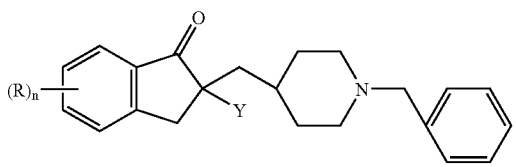

wherein R represents, the same as or different from each other, a hydrogen atom or a lower alkoxy group, n represents an integer of 1 to 4 and Y represents H or F, which comprises reacting the compound of the formula I with a benzyl halide.

Lower alkoxy group herein means a straight or branched lower alkyl group having 1 to 6 carbon atoms bonded with oxygen atom.

The halide is selected from chloride, bromide and iodide. The preferable halide is chloride or bromide.

The compounds of the formula II, wherein n is 1-3, R is methoxy or ethoxy and Y is H are preferred compounds.

Lower alkoxy group herein means a straight or branched lower alkyl group having 1 to 6 carbon atoms bonded with oxygen atom.

DETAILED DESCRIPTION OF THE INVENTION

The present invention provides a process for preparing compounds of the general formula I or a salt thereof:

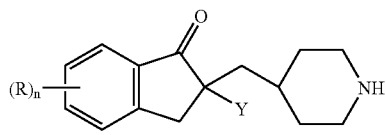

wherein R represents, the same as or different from each other, a hydrogen atom or a lower alkoxy group, n represents an integer of 1 to 4 and Y represents H or F, which comprises the selective hydrogenation of the compound of the general formula II:

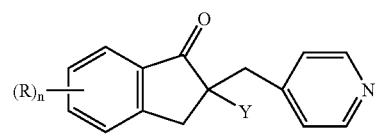

wherein R, n and Y have the same meaning as defined above and optionally converting the compound of the formula I to the salt.

Lower alkoxy group herein means a straight or branched lower alkyl group having 1 to 6 carbon atoms bonded with oxygen atom; methoxy, ethoxy and 5,6-dimethoxy groups being preferable.

The selective hydrogenation is carried out employing platinum oxide, palladium-carbon, raney nickel or ruthenium oxide catalyst. Platinum oxide is particularly preferred catalyst.

The hydrogenation takes place in a suitable solvent in the presence of an acid under a hydrogen pressure of 1 to 10 bars, preferably of 1 to 6 bars and more preferably of 1 to 4 bars at the temperature of 15° C. to 100° C., preferably of 20° C. to 35° C.

Examples of the suitable solvents for the hydrogenation are alcohols such as methanol or ethanol, acetonitrile, tetrahydrofuran, dimethylformamide, dimethylsulfoxide, dioxane, aromatic hydrocarbons such as benzene, toluene, xylene, etc., halogenated hydrocarbons such as dichloromethane, chloroform, carbontetrachloride, etc., ketones such as acetone, methyl ethyl ketone, ethyl isobutyl ketone, etc., ethers such as tert-butyl methyl ether, or carboxylates such ethyl acetate. A mixture of the solvents may also be used.

Preferable acid used in the hydrogenation is hydrochloric acid, sulfuric acid, phosphoric acid or acetic acid. Hydrochloric acid is more preferred and the product obtained is hydrochloric acid salt if the acid used is hydrochloric acid.

Hydrogenation is carried out in a conventional manner known in the art. Hydrogen gas is usually introduced into a hydrogenation flask containing the compound of the formula II, the solvent, the acid and the catalyst.

Utilizing the preferred temperature and pressure values, hydrogenation generally takes place in a few hours, e.g., from about 0.5 hour to about 36 hours.

When the hydrogenation is substantially complete, the desired product of the formula I is then isolated by standard methods, e.g., the catalyst is removed by filtration, the solvent evaporated and the product purified, if desired, by well-known methods such as crystallization or by chromatography.

The catalyst is usually present in an amount from about 0.01 to about 25 weight-percent, and preferably from about 0.1 to about 10 weight-percent, based on the compound of the formula II.

The compounds of the formula I, wherein n is 1-3, R is methoxy or ethoxy and Y is H are preferred compounds.

The preferred compounds of the formula I or the salts thereof are:
4-[(5,6-dimethoxy-1-indanon)-2-yl]methylpiperidine,
4-[(6-methoxy-1-indanon)-2-yl]methylpiperidine,
4-[(5-methoxy-1-indanon)-2-yl]methylpiperidine,
4-[(5,7-dimethoxy-1-indanon)-2-yl]methylpiperidne,
4-[(6,7-dimethoxy-1-indanon)-2-yl]methylpiperidne and
4-[(5,6-dimethoxy-2-fluoro-1-indanon)-2-yl]methylpiperidine.

The compounds of the formula I are useful for the preparation of the compounds of the formula III:

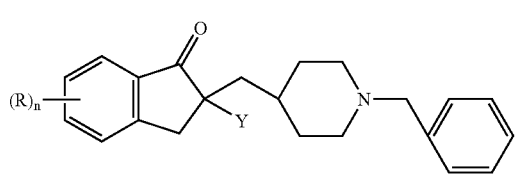

III wherein R represents, the same as or different from each other, a hydrogen atom or a lower alkoxy group, n represents an integer of 1 to 4 and Y represents H or F.

Lower alkoxy group herein means a straight or branched lower alkyl group having 1 to 6 carbon atoms bonded with oxygen atom; methoxy, ethoxy and 5,6-dimethoxy groups being preferable.

The compounds of the formula III can be prepared from the compounds of formula I by reacting the compounds of formula I with a benzyl halide. The halide is chloride, bromide or iodide. The preferable halide is chloride or bromide. The reaction steps for the synthesis of the compounds of the formula III are shown is the scheme shown below.

The compounds of the formula III, wherein n is 1-3, R is methoxy or ethoxy and Y is H are preferred compounds.

Lower alkoxy group herein means a straight or branched lower alkyl group having 1 to 6 carbon atoms bonded with oxygen atom, methoxy and 5,6-dimethoxy groups being preferable.

Preferred compounds of the formula III or the salts thereof are:
1-benzyl-4-[(5,6-dimethoxy-1-indanon)-2-yl]methylpiperidine,
1-benzyl-4-[(6-methoxy-1-indanon)-2-yl]methylpiperidine,
1-benzyl-4-[(5-methoxy-1-indanon)-2-yl]methylpiperidine,
1-benzyl-4-[(5,7-dimethoxy-1-indanon)-2-yl]methylpiperidne,
1-benzyl-4-[(6,7-dimethoxy-1-indanon)-2-yl]methylpiperidne and
1-benzyl-4-[(5,6-dimethoxy-2-fluoro-1-indanon)-2-yl]methylpiperidine.

Scheme:

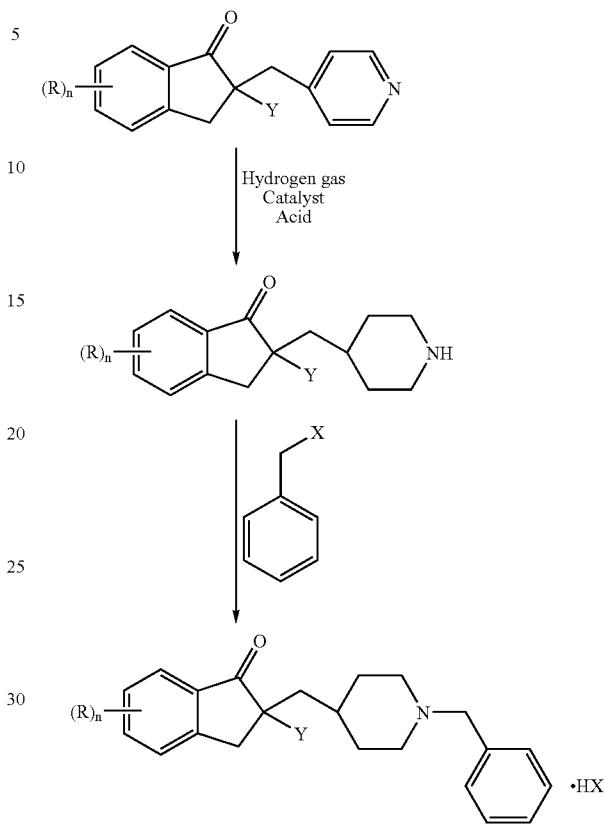

The invention will now be further described by the following examples, which are illustrative rather than limiting.

EXAMPLE 1

The mixture of 5,6-dimethoxy-2-(4-pyridyl)methylene-1-indanone (34 gm), methanol (325 ml), methylenedichloride (200 ml) and 5% palladium-charcoal (2 gm) is taken in a hydrogenation flask and subjected to hydrogenation under a hydrogen pressure of 2 bars for 3 hours. The catalyst is removed by filtration and the solvents are evaporated completely under vacuum to obtain a residue. Ethyl acetate (150 ml) is added to the residue and stirred for 20 minutes at 25° C. to 30° C. The contents are then cooled to 0° C., stirred for 30 minutes and filtered to give 34 gm of 5,6-dimethoxy-2-(4-pyridyl)methyl-1-indanone.

EXAMPLE 2

The mixture of 5,6-dimethoxy-2-(4-pyridyl)methyl-1-indanone (45 gm), methanol (600 ml), concentrated hydrochloric acid (18 ml) and platinum oxide catalyst (2.5 gm) is taken into a hydrogenation flask and subjected to hydrogenation under a hydrogen gas pressure of 2 bars for 5 hours. The catalyst is filtered off and the solvents are evaporated completely under vacuum. Ethyl acetate (150 ml) is added to the residue and stirred for 15 minutes at 25° C. to 30° C. Then the contents are cooled to 0° C., stirred for 30 minutes and filtered to give 48 gm of 4-[(5,6-dimethoxy-1-indanon)-2-yl]methylpiperidine hydrochloride.

EXAMPLE 3

Benzyl bromide (4.5 ml) is added to the mixture of 4-[(5,6-dimethoxy-1-indanon)-2-yl]methylpiperidine hydrochloride (8 gm), toluene (150 ml) and potassium carbonate (9 gm) and stirred for 2 hours at 25° C. 30° C. The reaction mass is cooled to 10° C. and filtered. The filtrate is washed with water, dried over sodium sulfate and concentrated under vacuum. Ethyl acetate (200 ml) is added to the residue, stirred for 10 minutes at 25° C. 30° C., cooled to 0° C. and hydrogen chloride gas is passed till the pH 2 is attained. The reaction is maintained for 30 minutes at the same temperature. The solid is filtered, washed with ethyl acetate and dried under vacuum at 50° C. for 4 hours to give 8 gm of donepezil hydrochloride.

We claim:

1. A process for the preparation of the compound of the general formula I or a salt thereof:

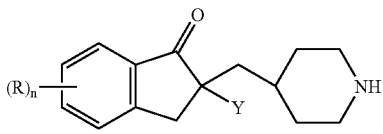
I wherein R represents, the same as or different from each other, a hydrogen atom or a lower alkoxy group, n represents an integer of 1 to 4 and Y represents H or F, which comprises hydrogenating the compound of the general formula II:

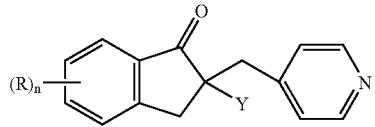
II wherein R, n and Y have the same meaning as defined above, with hydrogen using platinum oxide, palladium-carbon, raney nickel or ruthenium oxide catalyst in a solvent selected from the group consisting of alcohols, methanol, ethanol, acetonitrile, tetrahydrofuran, dimethylformamide, dimethylsulfoxide, dioxane, aromatic hydrocarbons, benzene, toluene, xylene, halogenated hydrocarbons, dichloromethane, chloroform, carbontetrachloride, ketones, acetone, methyl ethyl ketone, ethyl isobutyl ketone, ethers, tert-butyl methyl ether, carboxylates, ethyl acetate, and mixtures thereof, in the presence of an acid in the quantities ranging from 0.1 to 10 moles of the acid per mole of the compound of formula II, under a hydrogen pressure of 1 to 10 bars and optionally converting the compound of the formula I to the salt.

2. The process according to claim 1, wherein R is methoxy or ethoxy; n is 1-3; and Y is fluorine or hydrogen.

3. The process according to claim 1, wherein the compound of the formula I is 4-[(5,6-dimethoxy-1-indanon)-2-yl]methylpiperidine or a salt thereof.

4. The process according to claim 1, wherein 0.5 to 5.0 moles of the acid per mole of the compound of formula II is used.

5. The process according to claim 1, wherein the acid is selected from hydrochloric acid, sulfuric acid, phosphoric acid and acetic acid.

6. The process according to claim 5, wherein the acid is hydrochloric acid.

7. The process according to claim 1, wherein the catalyst is platinum oxide.

8. The process according to claim 1, wherein the pressure is about 1 to 6 bars.

9. The process according to claim 8, wherein the pressure is about 1 to 4 bars.

* * * * *